US005973829A

United States Patent [19]

Möller et al.

[11] Patent Number: 5,973,829

[45] Date of Patent: Oct. 26, 1999

[54] ILLUMINATING ARRANGEMENT FOR A SURGICAL MICROSCOPE

[75] Inventors: Gerhard Möller, Aalen; Joachim Steffen, Westhausen; Christian Lücke, Oberkochen, all of Germany

[73] Assignee: Carl-Zeiss-Stiftung, Heidenheim, Germany

[21] Appl. No.: 09/148,881

[22] Filed: Sep. 8, 1998

[30] Foreign Application Priority Data

Sep. 9, 1997 [DE] Germany ........................... 197 39 428

[51] Int. Cl.[6] ..................................................... G02B 21/06

[52] U.S. Cl. ........................... 359/389; 359/385; 359/388

[58] Field of Search ..................................... 359/368, 373, 359/375–381, 384–390, 227, 233–235; 351/216–218, 219, 233–236, 243

[56] References Cited

U.S. PATENT DOCUMENTS

| | | | |
|---|---|---|---|
| 4,209,226 | 6/1980 | Wardlaw et al. | 359/383 |
| 4,657,357 | 4/1987 | Nishimura et al. | 359/389 |
| 4,807,980 | 2/1989 | Dietrich et al. | 359/388 |
| 5,126,877 | 6/1992 | Biber | 359/389 |
| 5,515,209 | 5/1996 | Buchroeder et al. | 359/362 |
| 5,708,532 | 1/1998 | Wartmann | 359/362 |
| 5,748,367 | 5/1998 | Lucke et al. | 359/388 |

FOREIGN PATENT DOCUMENTS

| | | | |
|---|---|---|---|
| 3208706 | 11/1982 | Germany | 359/385 |
| 3427592 | 2/1986 | Germany | 359/385 |

*Primary Examiner*—Thong Nguyen
*Attorney, Agent, or Firm*—Walter Ottesen

[57] ABSTRACT

The invention is directed to an illuminating arrangement (5) for a surgical microscope (1) having an illuminating beam path (7) which runs essentially coaxially to the optical axis (9) of the surgical microscope. The illuminating arrangement (5) includes an optical ancillary element (15) having a positive refractive power. The ancillary element (15) can be selectively pivoted into and out of the illuminating beam path. The illuminating aperture in the region of the optical axis (9) of the surgical microscope (1) is increased by pivoting the optical ancillary element (15) into the illuminating beam path (7). This is done without changing the viewing focal intercept of the surgical microscope (1).

5 Claims, 2 Drawing Sheets

11 1 5 25 21 13 19 7 14 15 17 23 9 7 3

11

1
5
25
21
13
19
7
14
15
17
23

9
7
3

16
13
9
14
18

ILLUMINATING ARRANGEMENT FOR A SURGICAL MICROSCOPE

FIELD OF THE INVENTION

The invention relates to an illuminating arrangement for a surgical microscope having an illuminating beam path running essentially coaxially to the optical axis of the microscope.

BACKGROUND OF THE INVENTION

An illuminating arrangement of this kind is available commercially from Carl Zeiss under the product designation "Varioskop" together with the surgical microscope OPMI CS. In this known illuminating arrangement, even narrow surgical channels can be illuminated because of the illuminating beam path running essentially coaxially to the optical axis of the surgical microscope. The diameter of the illuminated area and the illumination intensity can be varied within certain limits.

Especially in neurosurgery, it has been shown to be desirable to further increase the illumination intensity for fluorescent excitation of tumorous tissue in order to be able to do without a special fluorescence illumination such as a hand-guided light conductor wherein light emanates from the end face thereof.

SUMMARY OF THE INVENTION

It is an object of the invention to provide an illuminating arrangement with which the intensity of illumination can be changed to a greater extent than heretofore.

The illuminating arrangement of the invention is for a surgical microscope defining an optical axis. The illuminating arrangement includes: illuminating optics defining an illuminating aperture and an illuminating beam path running essentially coaxial to the optical axis; an optical ancillary element having a positive refractive power; and, a device for selectively moving the optical ancillary element into and out of the illuminating beam path to thereby selectively increase the illuminating aperture in the region of the optical axis while the viewing focal intercept of the surgical microscope remains unchanged.

The object end aperture of the illuminating beams can be significantly increased in the region of the optical axis by means of the optical ancillary element of positive refractive power which can be introduced into the illuminating beam path in the course of surgery. This is done without it being necessary to change the intersection distance of the surgical microscope, that is, the working distance of the surgical microscope. For the illuminating arrangement of the invention, experiments have shown that the increase of illumination intensity makes possible a fluorescence excitation of the tumorous tissue utilizing a conventional surgical microscope light source. The increase in illumination intensity is obtained with the optical ancillary component arranged in the illuminating beam path. This optical ancillary element is illumination active.

There is a reduction of illumination intensity in the peripheral region of the illuminated area which is caused by the ancillary element which is introduced into the illuminating beam path and is therefore illumination active. This reduction in illumination intensity is acceptable because the ancillary element can be removed from the illuminating beam path after fluorescence excitation is completed.

In another embodiment, the illuminating arrangement images a light conductor end onto the observed object. In this way, the actual light source can be arranged at a distance from the surgical wound and the intensity of illumination can nonetheless be increased in a significant manner with the ancillary element according the feature of the invention.

Known illuminating arrangements can be retrofitted in a simple manner with the ancillary element when the illuminating arrangement includes a deflecting mirror which deflects the illuminating beam path to the observed object and when the ancillary element is mounted between the deflecting mirror and the observed object.

In a further embodiment of the invention, the ancillary element can be pivoted into and out of the illuminating beam path. In this way, an especially simple actuating mechanism results for the ancillary element.

If the illuminating arrangement includes a red attenuating filter, conventional light sources can be utilized for fluorescence excitation when the ancillary element is pivoted into the illuminating beam path or mounted in this path.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
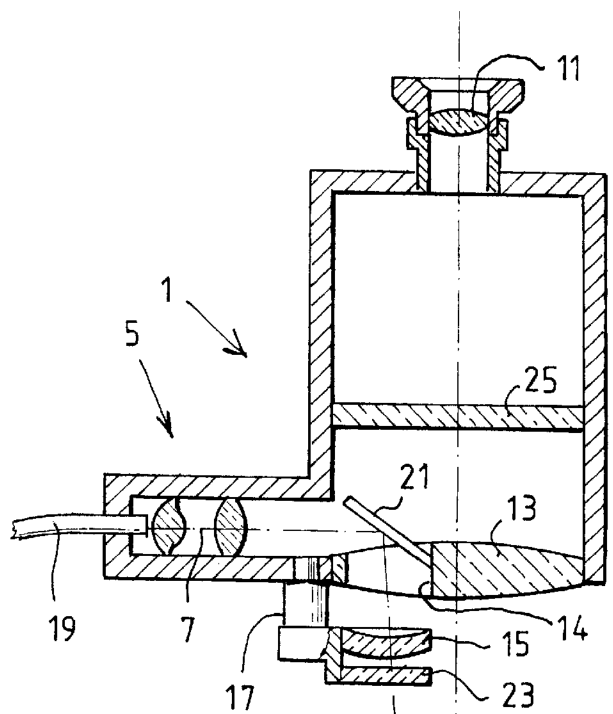
FIG. 1 is a side elevation view, in section, of an illuminating arrangement according to the invention which is integrated into a surgical microscope.

In FIG. 1, reference numeral 1 identifies a surgical microscope for viewing an observed object 3. An illuminating arrangement 5 is integrated into the surgical microscope 1 and the illuminating arrangement 5 has a beam path 7 which illuminates the observed object 3 essentially coaxially to the optical axis 9 of the surgical microscope. In this embodiment, the angle conjointly defined by the optical axis 9 and the illuminating beam path 7 is in a range of approximately 3° to approximately 6°.

The surgical microscope 1 is a stereomicroscope and includes an ocular tube 11 and a main objective 13 common to both viewing beam paths of the surgical microscope.

The illuminating arrangement 5 includes an optical ancillary element 15 which is held on a pivot lug 17. The pivot lug 17 permits a rotation about the axis thereof which runs essentially parallel to the optical axis 9 and therefore permits the optical ancillary element 15 to be pivoted into and out of the illuminating beam path 7.

The illuminating arrangement 5 conducts the illuminating light via optical elements to a deflecting mirror 21. The illuminating light comes from a separate light source (not shown) via a light conductor 19. The defecting mirror 21 deflects the illuminating beam path 7 in the direction toward the viewed object 3. The illuminating beam path 7 runs from the light conductor 19 to the deflecting mirror 21 transversely to the optical axis 9 of the surgical microscope 1.

The deflecting mirror 21 is mounted in a cutout 14 of the surgical microscope main objective 13 in order to direct the illuminating light toward the viewed object 3 as coaxially as possible to the optical axis 9.

The ancillary element 15 is shown in FIG. 1 in its pivoted in position wherein it is disposed in the illuminating beam path 7 and wherein it increases the illuminating aperture in the region of the optical axis. The ancillary element 15 and the red attenuating filter 23 are conjointly pivotally mounted on the pivot lug 17. With this combination of ancillary element 15 and red attenuating filter 23, the illuminating arrangement 5 can be used for fluorescence excitation of tumorous tissue of the viewed object 3. The tumorous tissue is pretreated with appropriate fluorescence markers. The ancillary element 15 increases the illuminating aperture and therefore increases the illumination intensity. An emission filter 25 is matched to the red attenuation filter 23. This emission filter 25 serves for viewing the fluorescent light emitted from the tumorous tissue as a consequence of the above and the filter 25 is mounted in the viewing beam path of the surgical microscope 1. The emission filter 25 filters out the excitation light which is passed by the red attenuating filter 23 and is shown schematically in FIG. 1.

For an alternate embodiment, the emission filter 25 can be pivoted in and out together with the optical ancillary element 15.

Figure 2:
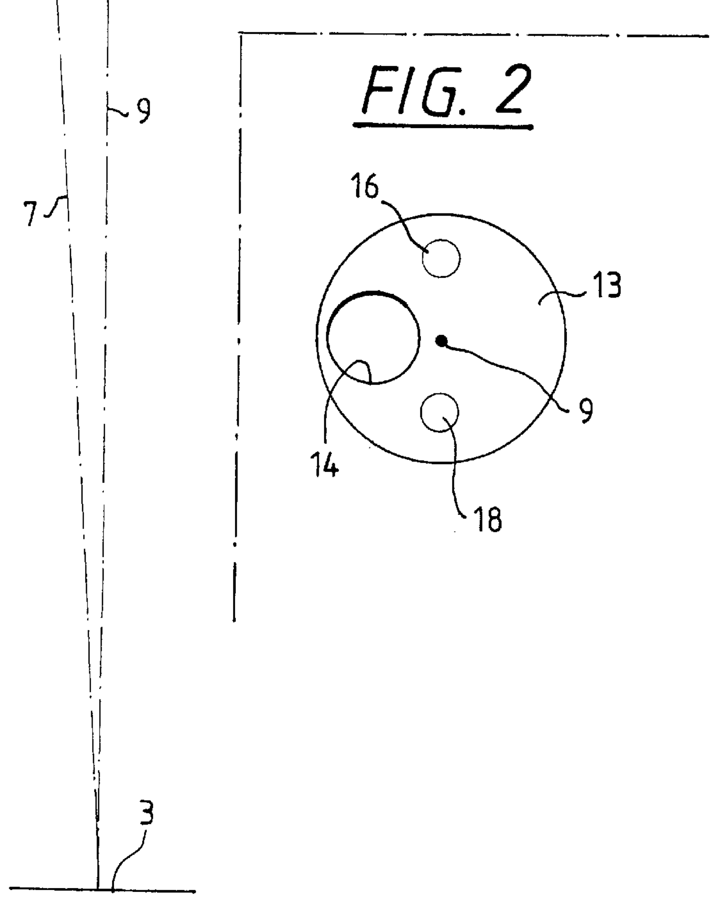
FIG. 2 is a plan view of the main objective of the surgical microscope shown in FIG. 1; and, FIG. 3 is an enlarged detail view of the optical elements of the illuminating arrangement of FIG. 1.

In FIG. 2, the main objective 13 of the surgical microscope 1 can be seen in plan view along the optical axis 9. Here, the position of the cutout 14 can be seen with reference to the regions 16 and 18 of the main objective 13 which are penetrated by the viewing rays.

Figure 3:
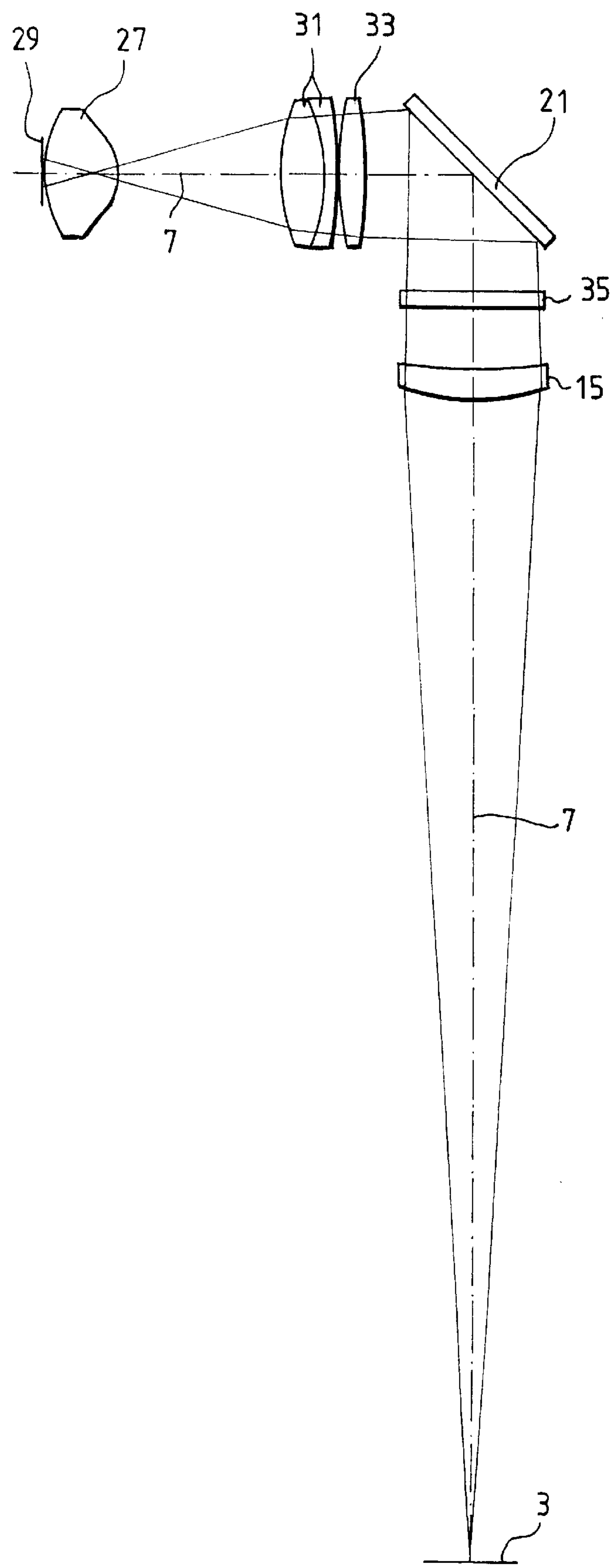

In FIG. 3, the optically effective components of the illuminating arrangement 5 are shown in detail.

This illuminating optic includes an aspherical lens 27 in direct proximity to the plane 29 of the light conductor exit face. A composite lens 31, which includes two individual lenses, and a lens 33 are arranged downstream of the aspheric lens 27. The deflecting mirror 21 follows the lens 33 in a direction toward the viewed object. The deflecting mirror 21 deflects the illuminating light through a plane-parallel glass plate 35 and the optical ancillary element 15 which is configured as a meniscus-shaped lens.

The precise optical data of this illuminating optic are presented in Table I. The numbers listed in the left-hand column correspond to respective optically-effective surfaces counted from the light conductor 19. Accordingly, number 1 is therefore the light-conductor exit plane 29 and number 2 is the surface of the aspherical lens 27 which faces toward the light conductor. Number 3 is the surface of aspheric lens 27 which faces toward the viewed object, et cetera. The term "radius" identifies the radius of curvature and the term "planar" indicates a radius of curvature of infinity. The term "thickness" identifies the particular spacing between the corresponding optically effective surfaces. The types of glass identified in the column entitled "glass" are product designations of SCHOTT GLAS of Mainz, Germany.

It is understood that the foregoing description is that of the preferred embodiments of the invention and that various changes and modifications may be made thereto without departing from the spirit and scope of the invention as defined in the appended claims.

TABLE I

| No. | Radius in mm | Thickness in mm | Glass | Optical Component |
|---|---|---|---|---|
| 1 | planar | .0010 | | Fiber (19) |
| 2 | 24.58200 | 14.80 | K5 | Asphere (27) f = 15.1 mm |
| 3 | −9.30570 | 32.80 | | |
| 4 | 53.47200 | 8.000 | SK2 | |
| 5 | −38.4040 | 3.500 | SF1 | Composite Lens (31) f = 80.3 mm |
| 6 | −175.290 | .1000 | | |
| 7 | 113.0100 | 4.500 | BK7 | Lens (33) f = 109.7 mm |
| 8 | −113.010 | 22.00 | | |
| 9 | planar | 23.00 | | Mirror (21) |
| 10 | planar | 3.000 | BK7 | Glass Plate (35) |

TABLE I-continued

| No. | Radius in mm | Thickness in mm | Glass | Optical Component |
|---|---|---|---|---|
| 11 | planar | 12.00 | | |
| 12 | −175.030 | 5.900 | B270 | Lens (15) f = 172.4 mm |
| 13 | −60.3600 | | | |

What is claimed is:

1. An illuminating arrangement for a surgical microscope having viewing optics defining a working distance, said viewing optics including an objective defining an optical axis and said objective having regions penetrated by viewing rays for viewing an object, the illuminating arrangement comprising:

illuminating optics defining an illuminating aperture and an illuminating beam path passing through said objective outside said regions and running almost coaxial to said optical axis;

said illuminating optics including a light conductor having an end face and an optical assembly for imaging said end face on said object;

an optical ancillary element having a positive refractive power; and, a device for selectively moving said optical ancillary element into and out of said illuminating beam path to selectively increase said illuminating aperture while at the same time avoiding an intersection with said viewing rays thereby leaving said working distance of said viewing optics of said surgical microscope unchanged.

2. The illuminating arrangement of claim 1, said optical assembly including a deflecting mirror for deflecting said illuminating beam path toward said object; and, said optical ancillary element being mounted between said deflecting mirror and said object.

3. The illuminating arrangement of claim 1, said illuminating arrangement further comprising a housing and said device being a pivot assembly mounted on said housing for pivoting said optical ancillary element into and out of said illuminating beam path.

4. The illuminating arrangement of claim 1, further comprising a red attenuation filter operatively connected to said device so as to be selectively movable into and out of said illuminating beam path.

5. The illuminating arrangement of claim 1, wherein said illuminating arrangement has the following optical data:

| No. | Radius in mm | Thickness in mm | Glass | Optical Component |
|---|---|---|---|---|
| 1 | planar | .0010 | | Fiber (19) |
| 2 | 24.58200 | 14.80 | K5 | Asphere (27) f = 15.1 mm |
| 3 | −9.30570 | 32.80 | | |
| 4 | 53.47200 | 8.000 | SK2 | |
| 5 | −38.4040 | 3.500 | SF1 | Composite Lens (31) f = 80.3 mm |
| 6 | −175.290 | .1000 | | |
| 7 | 113.0100 | 4.500 | BK7 | Lens (33) f = 109.7 mm |
| 8 | −113.010 | 22.00 | | |
| 9 | planar | 23.00 | | Mirror (21) |
| 10 | planar | 3.000 | BK7 | Glass Plate (35) |
| 11 | planar | 12.00 | | |
| 12 | −175.030 | 5.900 | B270 | Lens (15) f = 172.4 mm |
| 13 | −60.3600 | | | |

* * * * *